United States Patent
Walele et al.

(10) Patent No.: US 6,552,212 B2
(45) Date of Patent: Apr. 22, 2003

(54) BENZOATE ESTERS OF HYDROXYL TERMINATED POLYETHER POLYSILOXANE COPOLYOLS AND PROCESS FOR PRODUCING SAME

(75) Inventors: Ismail I. Walele, Saddle Brook, NJ (US); Samad A. Syed, Paramus, NJ (US)

(73) Assignee: Finetex, Inc., Elmwood Park, NJ (US)

( * ) Notice: Subject to any disclaimer, the term of this patent is extended or adjusted under 35 U.S.C. 154(b) by 0 days.

(21) Appl. No.: 09/854,852

(22) Filed: May 14, 2001

(65) Prior Publication Data

US 2003/0044371 A1 Mar. 6, 2003

(51) Int. Cl.$^7$ .................................................. C07F 7/08
(52) U.S. Cl. ..................... 556/437; 556/445; 424/70.12; 424/78.03
(58) Field of Search .................... 556/437, 445; 424/78.03, 70.12

(56) References Cited

U.S. PATENT DOCUMENTS

| | | |
|---|---|---|
| 4,275,222 A | 6/1981 | Scala, Jr. |
| 4,278,655 A | 7/1981 | Elmi |
| 4,293,544 A | 10/1981 | Elmi |
| 4,322,545 A | 3/1982 | Scala, Jr. |
| 4,323,693 A | 4/1982 | Scala, Jr. |
| 4,323,694 A | 4/1982 | Scala, Jr. |
| 4,654,161 A | 3/1987 | Kollmeier et al. |
| 4,717,498 A | 1/1988 | Maxon |
| 4,791,097 A | 12/1988 | Walele et al. |
| 4,960,845 A | 10/1990 | O'Lenick, Jr. |
| 5,008,103 A | 4/1991 | Raleigh et al. |
| 5,066,756 A | 11/1991 | Raleigh et al. |
| 5,070,168 A | 12/1991 | O'Lenick, Jr. |
| 5,070,171 A | 12/1991 | O'Lenick, Jr. |
| 5,073,619 A | 12/1991 | O'Lenick, Jr. |
| 5,098,979 A | 3/1992 | O'Lenick, Jr. |
| 5,120,812 A | 6/1992 | O'Lenick, Jr. |
| 5,136,063 A | 8/1992 | O'Lenick, Jr. |
| 5,149,765 A | 9/1992 | O'Lenick, Jr. |
| 5,153,294 A | 10/1992 | O'Lenick, Jr. |
| 5,166,297 A | 11/1992 | O'Lenick, Jr. |
| 5,196,499 A | 3/1993 | O'Lenick, Jr. |
| 5,226,923 A | 7/1993 | O'Lenick, Jr. |
| 5,237,035 A | 8/1993 | O'Lenick et al. |
| 5,248,783 A | 9/1993 | O'Lenick |
| 5,270,421 A | 12/1993 | Dordick et al. |
| 5,271,930 A | 12/1993 | Walele et al. |
| 5,280,099 A | 1/1994 | Imperante et al. |
| 5,292,847 A | 3/1994 | O'Lenick, Jr. |
| 5,296,625 A | 3/1994 | O'Lenick, Jr. et al. |
| 5,300,666 A | 4/1994 | Imperante et al. |
| 5,378,787 A | 1/1995 | Vrckounik et al. |
| 5,401,870 A | 3/1995 | Raleigh et al. |
| 5,451,692 A | 9/1995 | Raleigh et al. |
| 5,523,445 A * | 6/1996 | O'Lenick ..................... 556/440 |
| 5,656,664 A | 8/1997 | O'Lenick, Jr. |
| 5,658,558 A | 8/1997 | Schwartz |
| 5,705,147 A | 1/1998 | Shapiro et al. |
| 5,710,113 A | 1/1998 | Wells |
| 5,807,545 A | 9/1998 | Coffindafer et al. |
| 5,843,418 A | 12/1998 | Coffindafer et al. |
| 5,855,878 A | 1/1999 | Coffindafer et al. |
| 5,908,949 A * | 6/1999 | O'Lenick ..................... 556/437 |
| 5,939,058 A | 8/1999 | Schwartz |
| 6,004,542 A * | 12/1999 | O'Lenick ..................... 556/437 |
| 6,022,547 A | 2/2000 | Herb et al. |
| 6,030,630 A | 2/2000 | Fleury et al. |
| 6,346,595 B1 * | 2/2002 | O'Lenick ..................... 556/440 |

* cited by examiner

*Primary Examiner*—Paul F. Shaver
(74) *Attorney, Agent, or Firm*—Weingram & Associates, P.C.

(57) ABSTRACT

Compositions of matter comprising benzoate esters of hydroxyl terminated polyether polysiloxane copolyols, in particular dimethicone copolyol benzoates, and process for preparing same. The benzoate esters are useful for personal care cleansing products, such as bar and liquid soaps, skin and hair care products and textiles and fibers. The compounds are prepared by reacting benzoic acid with hydroxyl terminated polyether polysiloxane copolyols.

63 Claims, No Drawings

BENZOATE ESTERS OF HYDROXYL TERMINATED POLYETHER POLYSILOXANE COPOLYOLS AND PROCESS FOR PRODUCING SAME

BACKGROUND OF THE INVENTION

1. Field of the Invention

This invention relates generally to improved ester compositions, and more particularly to novel benzoate esters of hydroxyl terminated polyether polysiloxane copolyols, their process of manufacture and their use as a cosmetic ingredient for toiletry and cosmetic formulations. The esters are useful for personal care cleansing products, such as skin and hair care products, and bar and liquid soaps.

2. Description of the Related Art

Esters and acids are known for a variety of different applications for cosmetic, pharmaceutical and medicinal purposes. Benzoate esters of certain alcohols and alcohol mixtures, and their uses are disclosed in assignee's U.S. Pat. Nos. 4,275,222, 4,322,545, 4,323,693, and 4,323,694 all to Scala, Jr.; U.S. Pat. Nos. 4,278,655, and 4,293,544 both to Elmi; and U.S. Pat. Nos. 5,271,930, 5270,421, and 4,791,097 all to Walele et al. The disclosures of these patents are incorporated herein by reference.

U.S. Pat. Nos. 5,807,545; 5,843,418, and 5,855,878 to Coffindaffer et al. disclose a vehicle system having a thickening system which comprises a nonionic long-chain alkylated water-soluble polymer and a specific cationic quaternary ammonium surfactant component dispersed in a compatible solvent. The vehicle system is used to deliver an active component to the hair or skin. Compositions containing said vehicle system may additionally contain a hair setting agent, a distributing aid, and a surfactant. Polysiloxanes and other silicone compounds are useful as hair conditioning components in the compositions of the invention.

U.S. Pat. No. 6,030,630 to Fleury et al. discloses a cosmetic composition for the hair and/or skin comprising at least one water-dispersible sulfonated copolyester containing polyorganosiloxane units incorporating a plurality of repeating sulfonated polyester units and polyorganosiloxane units.

U.S. Pat. No. 5,136,063 to O'Lenick, Jr. discloses silicone fatty esters prepared by esterification of a fatty carboxylic acid, ester or anhydride and a hydroxy containing silicone compound. Examples of suitable reactants are fatty acids such as lauric, myristic, stearic, oleic, and linoleic acid. These are esters of fatty acids, i.e., aliphatic long chain fatty carboxylic acids.

U.S. Pat. No. 5,166,297 to O'Lenick, Jr. discloses a dimethicone copolyol halo ester intermediate which is useful for reaction with amines to prepare silicone based quaternary compounds.

U.S. Pat. No. 5,226,923 to O'Lenick, Jr. discloses processes for treating fiber with silicone fatty esters which act as conditioning agents for hair, skin, textile and other fibers. The silicone fatty esters are prepared by reacting the hydroxyl group in a silicone polymer with a fatty carboxylic acid, ester or anhydride, preferably in the presence of a catalyst. Examples of suitable reactants are fatty acids such as lauric, myristic, stearic, oleic, linoleic, and hydroxystearic.

U.S. Pat. No. 5292,847 To O'Lenick, Jr. discloses a series of silicone alkoxylates prepared by reacting a carboxy functional silicone and an ethylene oxide, propylene oxide or mixtures thereof. The products provide surfactant properties, specifically emulsification properties for many oil phases.

U.S. Pat. No. 5,296,625 to O'Lenick, Jr. et al. discloses a series of silicone alkoxylated esters which contain terminal carboxyl groups. The compounds are prepared by reacting the hydroxyl group in a silicone polymer with an anhydride. The compounds provide softening and lubrication when applied to fibers.

U.S. Pat. No. 5,378,787 to Vrckovnik et al. discloses a series of silicone reactive amino containing dimethicone copolyols. The amino silicone polymers are made by reacting an amino trialkoxy silane and a silanol to make an intermediate which is subsequently reacted with a dimethicone copolyol in the presence of alkaline catalyst. The reactive group is selected from silanol hydroxyl and optionally an alkoxy group.

U.S. Pat. No. 5,656,664 to O'Lenick, Jr. discloses esters prepared by reacting an alpha methyl alcohol and a fatty acid. A preferred ester is prepared using guerbet alcohols. The esters are useful as conditioning agents for skin.

U.S. Pat. Nos. 5,008,103 and 5,066,756 to Raleigh et al. disclose polysiloxane polymers containing organic polyether groups which are polysiloxane surface active agents for use in sun screen oils, antiperspirants, and the like.

U.S. Pat. No. 5,401,870 and 5,451,692 to Raleigh et al. disclose polysiloxane copolymers which are long chain hydrocarbon-modified polydiorganosiloxane polyoxyalkylene copolymers containing polydimethylsiloxy groups. The compounds are useful as emulsifiers in improved stability water-in-oil emulsions.

U.S. Pat. Nos. 5,658,558 and 5,939,058 to Schwartz disclose hair styling compositions containing at least one acrylic hair fixative resin and one or more plasticizing compounds selected from polycarboxylic acid esters and dimethicone copolyols.

U.S. Pat. No. 5,705,147 to Shapiro et al. discloses hair conditioning compositions comprising a mixture prepared by transesterification of a triglyceride with sucrose, and further comprising surfactants and optional ingredients such as polyether siloxane copolymers.

U.S. Pat. No. 5,710,113 to Wells discloses hair conditioning compositions containing a silicone fluid hair conditioning composition and silicone resin.

U.S. Pat. No. 6,022,547 to Herb et al. discloses a water-in-oil-in-water compositions including silicone-based surfactants comprising a dimethicone copolyol.

U.S. Pat. No. 4,654,161 to Kollmeier et al. discloses oxganopolysiloxanes that have one or more betaine groups, processes for their synthesis, and their use in cosmetic preparations.

U.S. Pat. No. 4,717,498 to Maxon et al. discloses dimethicone copolyol sulfosuccinate compounds obtained by reacting the ethoxylated polyether side chains of dimethicone copolyol with maleic anhydride to form a monester and then converting the monester to a sulfosuccinate by sulfonation of the double bond with a metallic sulfite, an amine or with a combination of a metallic sulfite and an amine. The compounds are useful as surfactants for improving the mildness and foam enhancing and stabilizing properties of shampoos and other personal care products.

U.S. Pat. No. 4,960,845 to O'Lenick, Jr. discloses sulfated silicone polymers which have the sulfate group on a pendant functionality rather than within the polymer backbone. The compounds provide a high level of foam in aqueous solution.

U.S. Pat. No. 5,070,168 to O'Lenick, Jr. discloses amino functional silicone polymers which have an ether amino pendant group. The compounds are prepared by introduction of an amino group on to the silicone pendant group. The compounds provide softness and lubrication to substrates.

U.S. Pat. No. 5,070,171 to O'Lenick, Jr. discloses organofunctional silicone polymers which have a phosphate pendant functionality present within the polymer. The phosphated silicone polymers are prepared by phosphation of a hydroxyl group on the silicone polymer.

U.S. Pat. No. 5,073,619 to O'Lenick, Jr. discloses organofunctional silicone polymers which have an amphoteric pendant functionality. The silicone amphoteric polymers are prepared by introduction of an amphoteric group by reaction of acrylic acid or methyl acrylate with a primary alkoxylated amine containing the silicone polymer. The compounds are good detergents and foaming agents.

U.S. Pat. No. 5,098,979 to O'Lenick, Jr. discloses quaternary silicone polymers useful in softening hair and fiber, and in conditioning skin. The compounds are silicone polymers which contain a quaternary nitrogen pendant group.

U.S. Pat. No. 5,120,812 to O'Lenick, Jr. discloses a vinyl silicone monomer which contains urethane functional groups, prepared by reaction of hydroxy containing silicone compounds with Benzene-1-(1-isocyanato-1-methylethyl)-3-(1-methylethenyl). The materials are used as intermediates in the preparation of polymers.

U.S. Pat. No. 5,149,765 to O'Lenick, Jr. discloses a silicone phosphate compound prepared by the phosphation reaction of a terminal hydroxy group of a silicone polymer with a phosphating agent selected from the group consisting of polyphosphoric acid and phosphorus pentoxide. The compounds useful as raw materials are terminal dimethicone copolyols. The compounds of the invention provide a lubricant antistat which can be applied to a variety of fibers.

U.S. Pat. No. 5,153,294 to O'Lenick, Jr. discloses a series of ester containing quaternary silicone polymers prepared by the esterification reaction of chloroacetic acid with a pendant hydroxyl group which is present on a silicone polymer. Preferably, the hydroxy containing silicone polymer has been alkoxylated with ethylene oxide, propylene oxide, or mixtures thereof. The compounds are useful in softening hair, and fiber and conditioning skin.

U.S. Pat. No. 5,196,499 to O'Lenick, Jr. discloses a series of silicone ester quaternary polymers. The compounds are prepared by the esterification of a terminal hydroxy group which is present on a silicone polymer with monochloracetic acid, and subsequently reacting the chloro ester so produced with a tertiary amine to produce the desired quaternary compound. The compounds are substantive to fiber and provide softening properties to fibers, hair and skin.

U.S. Pat. No. 5,237,035 to O'Lenick, Jr. discloses silicone phospholipid polymers which are lubricants, have high levels of foam, and low irritation properties. The compounds are prepared by phosphation of terminal dimethicone copolyols, followed by reaction with epichlorohydrin followed by reaction with amines.

U.S. Pat. No. 5,248,783 to O'Lenick discloses silicone alkoxylated ester salts which contain terminal carboxyl groups which have been neutralized with various fatty amine compounds. The compounds are prepared by reacting the hydroxyl group in a silicone polymer with an anhydride, followed by neutralization with an amine. The compounds provide high dense foam and solubility in many organic solvents.

U.S. Pat. No. 5,280,099 to Imperante et al. discloses taurinie functional silicone polymers, useful in softening hair and fiber and conditioning skin. The compounds are prepared by reacting chloro silicone intermediate with a taurine derivative. In a preferred embodiment, the hydroxy containing silicone polymer has been alkoxylated with ethylene oxide, propylene oxide or mixtures thereof.

U.S. Pat. No. 5,300,666 to Imperante et al. discloses silicone isethionate polymers useful as detergents and softeners. The compounds are prepared by the reaction of a carboxy silicone with an isethionate to produce surface active materials useful in personal care applications such as soap bars.

However, none of these references teach or suggest the specific novel benzoate esters of hydroxyl terminated polyether polysiloxane copolyols of this invention or the use of such ester compositions as emollients, moisturizers, sunscreen vehicles/solvents, hair conditioners and detanglers, wetting agents for powders, de-oilers/degreasers, emulsifiers/co-emulsifiers, viscosity-modifiers, foam-modifiers, facial cleansers, etc.

OBJECTS AND SUMMARY OF THE INVENTION

It is an object of this invention to provide novel benzoate esters of hydroxyl terminated polyether polysiloxane copolyols having unique properties which make them uniquely suitable for use in cosmetics, skin care products, personal care products such as body washes, cleansers, creams, lotions, shampoos, and other topical applications and products.

Another object of the invention is to produce benzoate esters of hydroxyl terminated polyether polysiloxane copolyols which are useful for treating textiles and fibers.

It is a further object of this invention to provide benzoate esters of hydroxyl terminated polyether polysiloxane copolyols having superior properties, namely superior foam characteristics and skin feel as compared to other benzoate esters, These and other objects are obtained by reacting benzoic acid with a hydroxyl terminated polyether polysiloxane copolyol. The compositions provided include many unique effects as compared to commercially available benzoate ester products.

DETAILED DESCRIPTION OF THE INVENTION

The novel benzoate esters of this invention have unique properties in that they are substantially non-greasy, lack oiliness and greasiness, have low pour points, have a bland odor, low toxicity and are stable. These properties make the compositions useful as a vehicle or carrier, emollient or solubilizer for toiletry and cosmetic formulations such as hair creams, hand cleaners, bath oils, suntan oils, antiperspirants, perfumes, colognes, cold creams, electric preshaves, eye and throat oils, finger nail polish, topical pharmaceutical ointments, lipsticks, stick rouge, skin lotions and creams, skin moisturizers, cleansing creams, and after bath splash and lotions, as well as other formulations.

A particularly useful composition of this invention, particularly for use in anti-perspirant compositions, sun screening compositions, perfumes, hair creams, hand cleaners, bath oils, suntan oils, 2 in 1 clear conditioning shampoos, clear conditioning shampoos, clear and mild skin cleansing gels, pearlescent hand soaps, bar soaps, creams and lotions for skin care, and the like, consists of a benzoate ester of hydroxyl terminated polyether polysiloxane co-polyols.

The hydroxyl terminated polyether polysiloxane co-polyols useful in making the benzoate esters of this invention may be represented by the following formula:

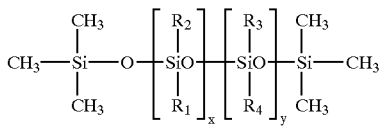

Formula I

In the above formula, x and y are each individually a number of one or greater, and preferably, each individually may be a number from 1 to 50.

$R_1$, $R_2$, $R_3$ and $R_4$ may all be the same or different, provided that at least one of $R_1$, $R_2$, $R_3$ or $R_4$ is a hydroxyl terminated polyether group, and preferably a hydroxyl terminated co-polyether group wherein one polyether group comprises ethylene oxide groups and the other polyether group comprises propylene oxide groups and mixtures thereof. Generally, the alkoxy groups of the polyether will be an ethylene oxide or propylene oxide.

The hydroxyl terminated polyether groups may be represented by the following structure:

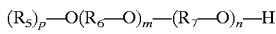

Formula II wherein $R_5$ may be an alkyl group of one to ten carbon atoms; p is a number from one to ten; $R_6$ is an alkyl group of from two to twelve carbon atoms; m is a number from one to twenty; $R_7$ is an alkyl group of from two to twenty carbon atoms; and n is a number from one to twenty.

When one of $R_1$, $R_2$, $R_3$ and $R_4$ is a hydroxyl terminated polyether as set forth above, the others may be selected from the group consisting of alkyl, aryl, alkaryl, aralkyl, alkoxy, substituted alkyl, substituted aryl, and mixtures thereof.

It is preferred that $R_1$, $R_1$, $R_3$ and $R_4$ be methyl or di-methyl provided that at least one of $R_1$, $R_2$, $R_3$ and $R_4$ is a hydroxyl terminated polyether copolyol radical. In a preferred embodiment, the polyether polysiloxane copolyol will conform to the following formula, wherein $R_1$, $R_2$, and $R_3$ are methyl groups:

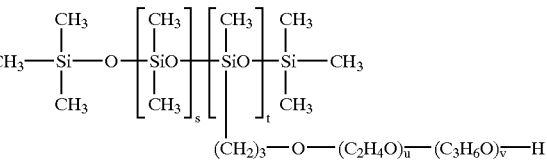

Formula III wherein s, t, u and v are each independently an integer of 1 or greater or the polyether polysiloxane copolyol may have the structure:

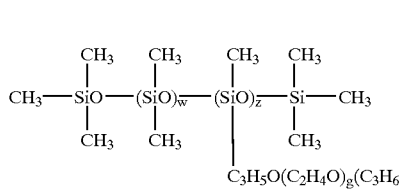

Formula IV wherein w and z are each independently an integer ranging from about 1 to 20 and g and h are each independently an integer ranging from about 1 to 50.

The hydroxyl terminated polyether polysiloxane copolyols useful in making the benzoate esters of this invention have the CTFA name of dimethicone copolyol and are also known as silicone glycol copolymer or polysiloxane polyether copolymers.

The hydroxyl terminated polyether polysiloxane copolyols useful in making the benzoate esters of this invention may be obtained from Union Carbide Chemicals and Plastics Company Inc. of Danbury, Conn. 06817 and are sold as SILWET® surfactants by OSI Specialties Company, Greenwich, Conn. The preferred hydroxyl terminated polyether polysiloxane copolyols are SILWET® L-7200, L-7210, L-7230, L-7604, L-7608, L-7614 and L-7657 silicone glycol copolymers. Silwet Surfactants L-7200, L-7210 and L-7230 are alkyl pendant polyether-modified silicone copolymers, namely hydroxy terminated copolymers.

Table A compares solubility characteristics of seven benzoate esters of SILWET® L-7200, L-7210, L-7230, L-7604, L-7608, L-7614 and L-7657 silicone glycol copolymers.

TABLE A

Benzoate Esters of SILWET ® Surfactants

| | 1 | 2 | 3 | 4 | 5 | 6 | 7 |
|---|---|---|---|---|---|---|---|
| | | | | Silwet ® Grade L-Series: | | | |
| | 7200 | 7210 | 7230 | 7604 | 7608 | 7614 | 7657 |
| Expt. R & D # Preparation | 103–109 | 104–24 | 103–113 | 103–112 | 104–39 | 104–26 | 104–36 |
| Solubility in Solvent: | | | | | | | |
| (1 gm. Product in 10 gm. Solvent): | | | | | | | |
| Water | + | – | + | + | – | + | + |
| Propylene Glycol | + | – | – | + | – | + | + |
| Ethanol | + | + | + | + | + | + | + |
| Glycerine | + | –vis. | –vis. | –vis. | –vis. | –vis. | –vis. |
| Finsolv TN | – | + | + | – | + | – | – |
| Finsolv P | – | + | + | + | – | – | + |
| Finsolv EMG-20 | + | – | – | – | + | + | + |
| Finsolv PL-62 | + | + | + | + | + | + | + |
| Finsolv PL-355 | + | + | + | + | + | + | + |
| Mineral Oil | – | – | – | – | – | – | – |
| DC 244-Volatile Silicone | – | – | – | – | – | – | – |

*By "–vis" is meant not soluble but viscous dispersion is formed.
**No. 3 is FINSOLV® SLB-101 and No. 4 is FINSOLV® SLB-201; the remaining Ex. Nos. are other benzoate esters.

The hydroxyl terminated polyether polysiloxane copolyols may also be obtained from Dow Corning (Midland, Michigan) as Dow Corning® 190 and 193 surfactants (Formula IV above).

The hydroxyl terminated polyether polysiloxane copolyols are also available from Goldschmidt Chemical Co., Inc. of Hopewel, Va., USA as ABIL® B 8842, 8843, 8847, ABIL® B 88183 and others (Formula III). ABIL® polyether siloxanes are block copolymers comprising a linear or branched-chain polysiloxane block and one or more polyether blocks.

In manufacturing the compounds of this invention, a benzoic acid is reacted with the hydroxyl terminated polyether polysiloxane copolyol.

Generally, the benzoic acid is reacted with the hydroxyl terminated polyether polysiloxane copolyol in stoichiometric amounts with a slight excess of the benzoic acid present. The starting materials are usually employed in stoichiometric proportions, but may be employed in amounts corresponding to from 1 to 1, and most preferably from 1 to 0.8, but can go as low as 1 to 0.5 with excellent results. The reaction may be carried out batchwise or in a continuous manner. A batch process is preferred.

A catalyst is present during the reaction. Among the catalysts which may be used are stannous oxalate, methane sulfonic acid, and the like.

The reaction is preferably conducted under an inert atmosphere of nitrogen at a reaction temperature of from 200° C. to 300° C., and preferably from 210° to about 235° C., and most preferably from 220° C. to 230° C. The acid value of the reaction is determined by procedures well known in the art. A reduced acid value indicates completion of esterification. When the acid value indicates that substantially all of the benzoic acid has been consumed, the reaction mass is then cooled to between about 100° and 130° C., and preferably from about 110° to 120° C., treated with Hydrogen Peroxide and then further cooled to about 25° C. or greater. The reaction mass is then filtered using filter aids such as diatomaceous earth, cellulose, or a silicate type filter aid and the like. The products of the reaction are a clear colorless to light yellow liquids.

The preferred benzoate esters of the invention are Dimethicone PEG/PPG-20/23 Benzoate (referred to herein as FINSOLV® SLB-101) and Dimethicone PEG-8 Benzoate (referred to herein as FINSOLV® SLB-201).

In a specific embodiment, and by way of illustration, this invention contemplates the production of benzoate esters of hydroxyl terminated polyether polysiloxane copolyols in accordance with the following equation to produce FINSOLV® SLB-101:

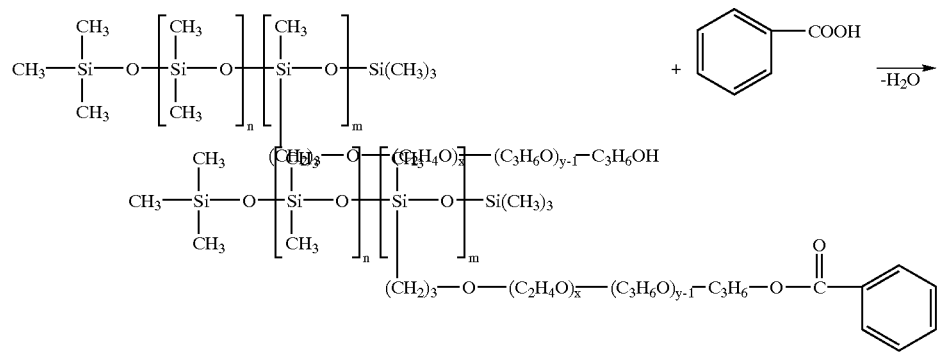

(Dimethicone Polyol (Cas #68937-55-3)+Benzoic Acid→Dimethicone Copolyo Benzoate (or Dimethicone PEG/PPG-20/23 Benzoate, i.e., FINSOLV® SLB-101)
(Dimethicone Polyol (Cas #68937-55-3) +Benzoic Acid→Dimethicone Copolyol Benzoate (or Dimethicone PEG/PPG-20/23 Benzoate, i.e., FINSOLV® SLB-101)

In a second specific embodiment, and by way of illustration, this invention contemplates the production of benzoate esters of hydroxyl terminated polyether polysiloxane copolyols in accordance with the following equation to produce FINSOLV® SLB-201:

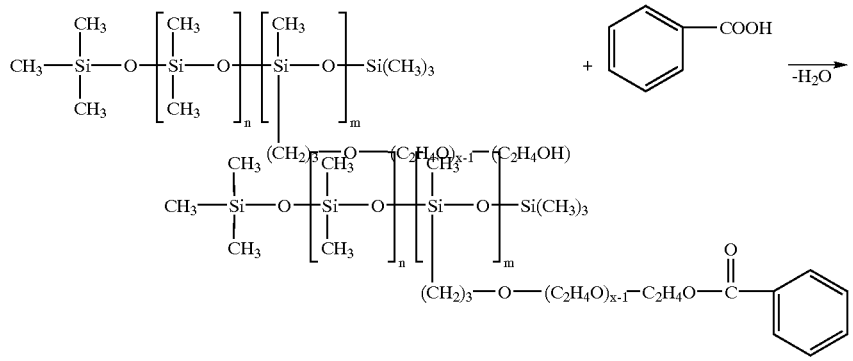

(Dimethicone Polyol (CAS #68937-54-2) +Benzoic Acid (CAS #65-85-0)→Dimethicone Copolyol Benzoate (or Dimethicone PEG-8-Benzoate, i.e., FINSOLV® SLB-201)

The preferred benzoate esters of the invention, FINSOLV® SLB-101 and FINSOLV® SLB-201, are based on a selected, but different, range of molecular weights of varying ratios of EO/PO (Ethylene Oxide/Propylene Oxide). The backbones of these two benzoate esters are EO/PO on a silicone glycol. They are highly hydrophilic and are designed to be used in aqueous systems where clarity and/or high degree of emollient solubility is desirable. Typical properties of the benzoate esters of the invention are described in Table B.

TABLE B

TYPICAL PROPERTIES OF BENZOATE ESTERS OF THE INVENTION

| Properties | FINSOLV ® SLB-101 | FINSOLV ® SLB-201 |
|---|---|---|
| Appearance | Clear, Viscous Liquid | Clear Slightly Viscous, Liquid |
| Actives | ≈100% | ≈100% |
| Odor | Mild | Mild |
| Viscosity, cps @ 25° C. | 3,500 | 700 |
| Refractive Index @ 21° C. | 1.4490 | 1.4540 |
| Surface Tension (dynes/cm) | 25.5 | 24.5 |
| Acidity, mg KOH/g | <1 | <1 |
| Moisture, % | <0.50 | <0.50 |
| Color, Gardner | 3 | <1 |

Table C below compares the solubility of the preferred benzoate esters of the invention in various solvents. The solubility is based on 1 gram of benzoate ester in 10 gm. solvent. Variations of properties and solubilities can be achieved by using different grades of SILWET® surfactants.

TABLE C

SOLUBILITY OF BENZOATE ESTERS OF THE INVENTION IN VARIOUS SOLVENTS

| Solvent | FINSOLV ® SLB-101 | FINSOLV ® SLB-201 |
|---|---|---|
| Water | Soluble | Soluble |
| Ethanol | Soluble | Soluble |
| Glycerine | Insoluble | Insoluble |
| Glycerine + Water (1:1) | Soluble | Soluble |
| Propylene Glycol | Insoluble | Soluble |
| Propylene Glycol + Water (1:1) | Soluble | Soluble |
| Volatile Silicones | Insoluble | Insoluble |
| Mineral Oil | Insoluble | Insoluble |
| FINSOLV ® TN | Soluble | Insoluble |
| FINSOLV ® EMG-20 + Water (1:1) | Soluble | Soluble |
| FINSOLV ® PL-62 | Soluble | Soluble |
| FINSOLV ® PL-355 | Soluble | Soluble |
| FINSOLV ® TN | Soluble | Insoluble |
| FINSOLV ® EMG-20 + Water (1:1) | Soluble | Soluble |
| FINSOLV ® PL-62 | Soluble | Soluble |
| FINSOLV ® PL-355 | Soluble | Soluble |

FINSOLV SLB-101 and FINSOLV SLB-201 are useful in all types of skin, hair and decorative products. Hand and face creams benefit from their unique feel on the skin and spreading properties. Bath and shower products as well as shampoos and conditioners, will have improved after-feel due to the specially selected silicone backbone. Color cosmetics will spread easier and have better wetting and leveling effects in the dispersion of pigments. Use of these esters at a very small level (0.1–0.5%) in bar soaps or syndet bar soaps imparts excellent skin feel without the soap feel. They also find use in skin care lotions, shaving soaps/foams, hair sprays and in perfumes/colognes.

FINSOLV® SLB-101 and FINSOLV® SLB-201 are also useful in the treatments of fibers, textiles and non-woven substrates such as tissues and wipes, lending a smooth, hydrophilic finish. Such substrates are used in skin cleansing applications.

The aforedescribed benzoate esters have the following properties:

1. Water solubility/dispersibility.
2. Ease of emulsification.
3. Emulsifier/co-emulsifier with other emollients.
4. Emolliency at body temperature with good after-feel.
5. Lack of greasiness, pleasant skin feel.
6. Lack of oiliness while imparting good lubrication.
7. Foam improvements.
8. Unusually low surface tension.
10. Bland odor.
11. Alcohol (ethanol) solubility.
12. Dispersibility in propylene glycol/glycerine/water.
13. Allows more water in some systems.
14. Low toxicity.
15. Acid, alkaline stability.
16. Solvents for many common skin and hair additives, including, sunscreens and over-the-counter therapy "actives".

Some of the benefits/advantages of the benzoates of hydroxyl terminated polyether polysiloxane copolyols of the invention are:

| Benefits | Advantages |
|---|---|
| Feel | Non-Oily |
| Detackification | Inert |
| Lubrication | Essentially non-toxic |
| Surface Tension Depressant | Non-sensitizing |
| Humectant | Stable |
| Softening | Inverse Solubility |

The benzoate esters of this invention are advantageous in that they are non-oily, tasteless, inert, essentially non-toxic and non-sensitizing, stable, and exhibit inverse solubility. They are hydrolytically stable and are soluble in water, alcohol and hydroalcoholic systems. For cosmetics and personal care products, they function in surface tension reduction, as wetting agents, and as emulsifiers/modifiers. For hair care products, they plasticize resins in hair spray, impart a silky feel to hair and aid in reduction of combing force, both wet and dry. In skin care products, they increase foam volume and the nature of the foam (bubble size, etc.), they improve wetting and lubricity of skin lotions, have lotions and creams/lathers.

The benzoate esters of this invention are useful as:

Emollients, solubilizers
Moisturizers, plasticizers
Sunscreen vehicles/solvents
Hair conditioners/detanglers
Wetting agents for powders (TiO$_2$, ZnO, etc.)
De-oilers/degreasers
Emulsifiers/co-emulsifiers
Foam-modifiers
Facial cleansers The foregoing list is only exemplary of the type of compositions in which the benzoate esters of this invention may be used and, as such, is not to be considered limiting.

The amount of benzoate ester used in an aqueous surfactant composition is dependent on the type of composition desired, the type and quantity of other ingredients used, e.g. cosmetic ingredients, and the amount and type of functional additives that are utilized. Typically, the amount of benzoate ester used ranges from about 0.5% to about 50% by weight of the aqueous surfactant composition. Preferably, from about 0.5% to about 5.0% of benzoate esters of this invention are used.

The aforementioned.benzoate esters have unique properties. In particular, they have foam modifying properties, which means that the benzoate esters of the invention confer any or all of the following properties upon a surfactant composition:

Flash foam increase;

Foam volume increase;

Foam viscosity increase or decrease;

Foam cell size increase or decrease.

While the particular foam modification is dependent upon the benzoate ester and surfactant of choice, none of the compounds suppress foam volume, i.e., none of the benzoate esters investigated are defoamers. Additionally, they have other properties which make them suitable for use as emollient carriers and for use as solvents.

The beenzoate esters of the invention are useful as foam modifiers for aqueous surfactant compositions such as hand cleaners, bath compositions, facial cleansers, cleansing creams, hard surface cleaners, shampoos, mousse products, shaving creams, pet cleaners, and concrete air-entrainment products.

Further, the benzoate esters of this invention possess other unusual physicochemical properties, in particular, low surface tension which can make them beneficial and unique components of sophisticated delivery systems such as in hand, face, and body creams and lotions.

The benzoate esters of this invention may be used in skin care compositions. The amount used in skin care compositions is dependent on the type of skin care compositions, the type and quantity of cosmetic ingredients used and the amount and type of functional additives. Typically the amount ranges from about 0.5% to about 80%, by weight, of the skin care compositions. For example, a facial cream may only have about 0.5%, where a massage oil may have up to about 80% by weight. Still higher amounts may be used in, for example, bath oils, e.g. 95%.

Further, the benzoate esters described herein may also function as plasticizers for polymers contained in skin care compositions, may be auxiliary suspending agents capable of assisting in the suspension of ingredients in skin care compositions and also may function as a dye leveling agent and dye carrier. Thus, the benzoate ester when used in skin care compositions serves not only as an emollient and carrier but also exhibits one or more other functions.

Table C is a Table of Identification which identifies products both known and produced by the process of this invention. For ease of identification each ester is identified by an internal Reference Number, and a Trade Name, where available. This identification system is used in the subsequent Tables and Examples.

TABLE C

Identification of Trade Names/INCI Names/Sources

1. FINSOLV ® SLB-101 (Dimethicone PEG/PPG-20/23 Benzoate)
   Invention Example Nos. 3 and 8
   (Source: Finetex Inc., Elmwood Park, NJ)

TABLE C-continued

Identification of Trade Names/INCI Names/Sources

2. FINSOLV ® SLB-102 (Dimethicone PEG-8 Benzoate)
   Invention Example Nos. 4 and 9
   (Source: Finetex Inc., Elmwood Park, NJ)
3. SCI = Sodium Cocoyl Isethionate
   TAURANOL ® I-78, TAURANOL ® I-78-6
   (Source: Finetex Inc., Elmwood Park, NJ)
4. Crothix = PEG 150 Pentaerythirtyl Tetrastearate
   (Source: Croda, Inc., Parsippany, NJ)
5. Germabel II = Prservative
   (Source: ISP - Sutton Labs, Wayne, NJ)
6. Glucamate SSE-20 = PEG-20 Methyl Glucose Sesquistearate
   (Source: Amerchol, Edison, NJ)
7. Silwet L Series = Dimethicone Copolyols
   (Source: OSI Specialties Co., Greenwich, CT)
8. FINSOLV ® PL-62 = Poloxamer 182 Dibenzoate
   (Source: Finetex Inc., Elmwood Park, NJ)
9. FINSOLV ® PL-355 = Poloxamer 105 Benzoate
   (Source: Finetex Inc., Elmwood Park, NJ)
10. FINSOLV ® EMG-20 = Methyl Gluceth-20 Benzoate
    (Source: Finetex Inc., Elmwood Park, NJ)
11. AMINOL ® HCA = Cocamide DEA
    (Source: Finetex Inc., Elmwood Park, NJ)
12. FINQUAT CT = Quaternium 75
    (Source: Finetex Inc., Elmwood Park, NJ)

Preparation of the esters of the invention is illustrated by the following non-limiting examples. In the examples, as well as throughout this application, the chemical and scientific symbols have their customary meanings and all percentages are weight percentages unless otherwise specified.

EXAMPLE #1

(Preparation of Benzoate Ester of Silicone Copolyol (Silwet-L-7200)

(Ref. No. 103–109)

In a 500 ml. four neck round bottom flask equipped with glass stirrer, distillation head, condenser and receiver, added 197.60 grams of Silwet L 7200 and 2.40 grams of Benzoic Acid. The temperature was raised to 60° C. with good flow of nitrogen. At 60C added 0.2 grams of Stannous Oxalate and continued to heat to 200° C. maintaining a good flow of nitrogen over 60 minutes. The reaction mixture was then raised to 220° C. in the next 30 minutes and held for three hours. The ester had the acidity of 0.20 mgs. KOH/g. The reaction product was treated with 1.0 gram of 35% Hydrogen Peroxide at 100° C. for one hour. The reaction product was cooled to 40° C. and treated with 0.2 grams each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 198 grams.

EXAMPLE #2

(Preparation of Benzoate Ester of Silicone Copolyol (Silwet-L-7200)

(Ref. No. 104.24)

In a 500 ml. four neck round bottom flask equipped with glass stirrer, distillation head, condenser and receiver, added 115 grams (1.0 moles) of Silwet-L-7200 and 2.4 grams (2.0 moles) of Benzoic Acid. The temperature was raised to 60° moles) of Benzoic Acid. The temperature was raised to 60° C. with good flow of nitrogen. At 60° C. added 0.1 grams of Stannous Oxalate and continued to heat to 200° C. maintaining a good flow of nitrogen over 60 minutes. The reaction mixture was then raised to 220° C. in the next 30 minutes and held for three hours. The ester had the acidity of 0.25 mgs. KOH/g. The reaction product was treated with 1.0 gram of 35% Hydrogen Peroxide at 100° C. for one hour. The reaction product was cooled to 40° C. and treated with 0.2 grams each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 117 grams.

EXAMPLE #3

(Preparation of Benzoate Ester of Silicone Copolyol (Silwet-L-7230)

(Ref. No. 103–113)

In a 500 ml. four neck round bottom flask equipped with glass stirrer, distillation head, condenser and receiver, added 198.0 grams of Silwet-L- 7230 and 2.0 grams of Benzoic Acid. The temperature was raised to 60° C. with good flow of nitrogen. At 60° C. added 0.2 grams of Stannous Oxalate and continued to heat to 200° C. maintaining a good flow of nitrogen over 60 minutes. The reaction mixture was then raised to 220° C. in the next 30 minutes and held for three hours. The ester had the acidity of 0.1 mgs. KOH/g. The reaction product was treated with 1.0 gram of 35% Hydrogen Peroxide at 100° C. for one hour. The reaction product was cooled to 40° C. and treated with 0.2 grams each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 199 grams.

EXAMPLE #4

(Preparation of Benzoate Ester of Silicone Copolyol (Silwet-L-7604)

(Ref. No. 103–112)

In a 500 ml. four neck round bottom flask equipped with glass stirrer, distillation head, condenser and receiver, added 193.5 grams of Silwet-L-7604 and 6.50 grams of Benzoic Acid. The temperature was raised to 60° C. with good flow of nitrogen. At 60° C. added 0.2 grams of Stannous Oxalate and continued to heat to 200° C. maintaining a good flow of nitrogen over 60 minutes. The reaction mixture was then raised to 220° C. in the next 30 minutes and held for three hours. The distillate collected was 0.90 grams against theoretical estimates of 0.96 grams. The ester had the acidity of 0.15 mgs. KOH/g. The reaction product was treated with 1.9 grams of 35% Hydrogen Peroxide at 100° C. for one hour. The reaction product was cooled to 40° C. and treated with 0.2 grams each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 198.5 grams.

EXAMPLE #5

(Preparation of Benzoate Ester of Silicone Copolyol (Silwet-L-7608)

(Ref. No. 104.39)

In a 500 ml. four neck round bottom flask equipped with glass stirrer, distillation head. condenser and receiver, added 249.06 grams (1.0 moles) of Silwet-L-7608 and 50.64 grams (1.0 mole) of Benzoic Acid. The temperature was raised to 60° C. with good flow of nitrogen. At 60° C. added 0.30 grams of Stannous Oxalate and continued to heat to 200° C. maintaining a good flow of nitrogen over 60 minutes. The reaction mixture was then raised to 220° C. in the next 30 minutes and held for three hours. The distillate collected was 7.0 grams against theoretical estimate of 7.47 grams. The ester had the acidity of 6.06 mgs. KOH/g. The reaction product was treated with 60 grams deionized water containing 6.0 grams Sodium Sulfate and 1.0 gram Sodium Carbonate at 80° C. The top layer containing the Benzoate Ester was collected. It was vacuum stripped at 115° C.–120° C. and 10–15 mm. of Hg Vacuum. The liquid benzoate ester of this reaction was then treated with 0.2 grams each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 255 grams.

EXAMPLE #6

(Preparation of Benzoate Ester of Silicone Copolyol (Silwet-L-7614)

(Ref. No. 104–26)

In a 500 ml. four neck round bottom flask equipped with glass stirrer, distillation head, condenser and receiver, added 150 grams (1.0 moles) of Silwet-L-7614 and 7.5 grams (2.0 moles) of Benzoic Acid. The temperature was raised to 60° C. with good flow of nitrogen. At 60° C. added 0.15 grams of Stannous Oxalate and continued to heat to 200° C. maintaining a good flow of nitrogen over 60 minutes. The reaction mixture was then raised to 220° C. in the next 30 minutes and held for three hours. The distillate collected was 1.05 grams against theoretical estimate of 1.10 grams. The ester had the acidity of 1.5 mgs. KOH/g. The reaction product was treated with 30 grams deionized water containing 6.0 grams Sodium Sulfate and 0.20 grams Sodium Carbonate at 80° C. The top layer containing the Benzoate Ester was collected. It was vacuum stripped at 115° C.–120° C. and 10–15 mm of Hg Vacuum. The liquid benzoate ester of this reaction was then treated with 0.1 gram each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 155 grams.

EXAMPLE #7

(Preparation of Benzoate Ester of Silicone Copolyol (Silwet-L-7657)

(Ref. No. 104–36)

In a 500 ml. four neck round bottom flask equipped with glass stirrer, distillation head, condenser and receiver, added 215.0 grams (1.0 moles) of Silwet-L-7657 and 5.53 grams (1.05 moles) of Benzoic Acid. The temperature was raised to 60° C. with good flow of nitrogen. At 60° C. added 0.22 grams of Stannous Oxalate and continued to heat to 200° C. maintaining a good flow of nitrogen over 60 minutes. The reaction mixture was then raised to 220° C. in the next 30 minutes and held for three hours. The distillate collected was 0.75 grams against theoretical estimate of 0.82 grams. The ester had the acidity of 0.72 mgs. KOH/g. The reaction product was treated with 1.0 gram of 35% hydrogen peroxide at 100° C. for one hours. The reaction product was cooled to 40° C. and treated with 0.2 grams each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 219 grams.

EXAMPLE #8

(Preparation of Benzoate Ester of Silicone Copolyol (Silwet-L-7230)

(Ref. No.: Larger Pilot Preparation)

To a stainless steel reactor vessel (of approximately 50 gal. capacity), equipped with high temperature heating (by hot oil) jacket, condenser and receiver, and mixing, Linder nitrogen, was charged added 398.4 lbs. of Silwet-L-7230 and 1.6 lbs. of Benzoic Acid. The temperature was raised to 60° C. with good flow of nitrogen. At 60° C. added 0.8 lbs. of Stannous Oxalate and continued to heat to 200° C. maintaining a good flow of nitrogen over 60 minutes. The reaction mixture was then raised to 220° C. in the next 30 minutes and held for three hours. The distillate collected was 0.21 lbs. against theoretical estimates of 0.23 lbs. The ester had the acidity of 0.20 mgs. KOH/g. The reaction product was treated with 0.5 lbs. of 35% hydrogen peroxide at 100° C. for one hour. The reaction product was cooled to 40° C. and treated with 0.4 lbs each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 399 lbs.

EXAMPLE #9

(Preparation of Benzoate Ester of Silicone Copolyol (Silwet-L-7604)

(Ref. No.: Larger Pilot Preparation)

To a stainless steel reactor vessel (of approximately 50 gal. capacity), equipped with high temperature heating (by hot oil) jacket, condenser and receiver, and mixing, under nitrogen, was charged added 388.16 lbs. (1.0 moles) of Silwet-L-7604 and 11.84 lbs. (1.0 moles) of Benzoic Acid. The temperature was raised to 60° C. with good flow of nitrogen. At 60° C. added 0.8 lbs. of Stannous Oxalate and continued to heat to 200° C. maintaining a good flow of nitrogen over 60 minutes. The reaction mixture was then raised to 220° C. in the next 30 minutes and held for three hours. The distillate collected was 1.70 lbs. against theoretical estimates of 1.74 lbs. The ester had the acidity of 0.10 mgs. KOH/g. The reaction product was treated with 0.5 lbs. of 35% hydrogen peroxide at 100° C. for one hour. The reaction product was cooled to 40° C. and treated with 0.4 lbs each of Magnesol (Synthetic Magnesium Silicate), Celatom 60 (diatomaceous earths) at 40° C. The product was filtered through a Filter Press with Whatman Paper #4 at 40° C. The net yield of the Benzoate Ester product was 399 lbs.

2 In 1 Clear Conditioning, Shampoos

Formulation I-A of Table 1 below is a common control formulation for 2 in 1 Clear Conditioning Shampoo. Formulations I-B and I-C of Table 1 are comparative formulations for the 2 in 1 Clear Conditioning Shampoo of Formulation I, the only differences being that 1.0% by wt. of Dimethicone Copolyol Benzoate is added to the control Formulation I-A with comparable adjustments to the percentage of water added. In Formulation I-B, FINSOLV® SLB-101 is added, and in Formulation I-C, FINSOLV® SLB-201 is added. Table I-A compares the properties of shampoo preparations of Formulations I-A, I-B and I-C. Table I-B compares foam results for shampoos of Formulations I-A, I-B and I-C. Table I-C compares the effects of shampoos of Formulations I-A, I-B and I-C on hair tresses.

TABLE I

FORMULATIONS I-A, I-B and I-C
2 IN 1 CLEAR CONDITIONING SHAMPOOS

| | % By Wt. | | |
|---|---|---|---|
| | Formulation I-A | Formulation I-B Ref. #: | Formulation I-C |
| Ingredients (INCI) | (122-233) | (222-235) | (122-234) |
| Water | 47.2 | 46.2 | 46.2 |
| Sodium Laureth Sulfate, 25% | 28.0 | 28.0 | 28.0 |
| Sodium Methyl Cocoyl Taurate[1] | 15.0 | 15.0 | 15.0 |
| Cocamide DEA | 4.0 | 4.0 | 4.0 |
| Quaternium 75 | 5.0 | 5.0 | 5.0 |
| Crothix | 0.3 | 0.3 | 0.3 |
| Fragrance Bouquet 39466 Intarome | 0.3 | 0.3 | 0.3 |
| FINSOLV ® SLB-101 | — | 1.0 | — |
| FINSOLV ® SLB-201 | — | — | 1.0 |
| Glydant Plus | 0.2 | 0.2 | 0.2 |
| Citric Acid, 25% to pH 6 | q.s. | q.s. | q.s. |

[1](TAURANOL ® WS CONC.), Finetex, Inc., Elmwood Park, NJ 07407

Procedure: Charge water and heat to 75° C. Add all ingredients in order. Cool to 45° C. Add Glydant Plus and fragrance. Cool to below 35° C. Package.

TABLE I-A

PROPERTIES OF 2 IN 1 CLEAR CONDITIONING SHAMPOO
PREPARATIONS OF FORMULATIONS I-A, I-B AND I-C

| Shampoo Preparation | Appearance | Clarity | pH | Viscosity (cps) |
|---|---|---|---|---|
| Formulation I-A (Control) | Clear, flowable gel | Clear | 6.0 | 7400 |
| Formulation I-B (Control + FINSOLV ® SLB-101) | Clear, thin, flowable gel | Clear | 6.0 | 1350 |
| Formulation I-C (Control + FINSOLV ® SLB-201) | Clear, flowable gel | Clear | 6.0 | 3300 |

TABLE I-B

FOAM RESULTS OF 2 IN 1 CLEAR CONDITIONING SHAMPOO
PREPARATIONS OF FORMULATIONS I-A, 1-B AND I-C

| Shampoo Preparation | Initial Volume Of Foam (mls) | Volume After 5 mins. (mls) | Foam Characteristics |
|---|---|---|---|
| Formulation I-A (Control) | 250 | 100 | Thin, loose, scattered, airy foam. Not compact. No soft feel. |
| Formulation I-B (Control + FINSOLV ® SLB-101) | 350 | 300 | Thick, dense rich foam. Compact foam. Soft feel. No air between bubbles. |
| Formulation I-C (Control + FINSOLV ® SLB-201) | 350 | 275 | Thick, dense rich foam. Compact. Soft & silky feel. No air between bubbles. |

Procedure: 1% of the product was dissolved in 200 mls. of water and shaken in a 500 mls cylinder with 10 sets of shakes.

TABLE I-C

COMPARISON OF EFFECTS OF 2 IN 1 CLEAR
CONDITIONING SHAMPOO PREPARATIONS OF
FORMULATIONS I-A, I-B AND I-C ON HAIR TRESSES

|  | Formulation I-A (Control) | Formulation I-B (Control + FINSOLV ® SLB-101) | Formulation I-C (Control + FINSOLV ® SLB-201) |
|---|---|---|---|
| DRY COMB | 4 | 1 | 2 |
| WET COMB | 6 | 3 | 4 |
| DETANGLING | 6 | 2 | 3 |
| SHINE/GLOSS | 10 | 1 | 2 |
| DRY FEEL/HANDLE | 6 | 2 | 3 |

Note:
All measurements are on a scale of 1–10, with 1 = best and 10 = worst)

Note: All measurements are on a scale of 1–10, with 1=best and 10=worst) Procedure: Rinsed hair tresses under tap water for 15 seconds. Rinsed hair tresses were treated with shampoo. Mixed for 5 minutes. Removed the tresses and rinsed with tap water running on it for 15 seconds. Air dried. Performed wet and dry comb tests.

Clear Conditioning Shampoos

Formulation II-A of Table II below is a common control formulation for Clear Conditioning Shampoo. Formulations II-B and II-C of Table II are comparative formulations for the Clear Conditioning Shampoo of Formulation II-A, the only differences being that 1.0% by wt. of Dimethicone Copolyol Benzoate is added, with comparable adjustments to the percentage of water added. In Formulation II-B, FINSOLV® SLB-101 is added, and in Formulation II-C, FINSOLV® SLB-201 is added. Table II-A compares the properties of shampoo preparations of Formulations I-A, I-B, and I-C. Table II-B compares foam results for shampoos of Formulations II-A, II-B and II-C. Table II-C compares the effects of shampoos of Formulations II-A, II-B and II-C on hair tresses.

TABLE II

FORMULATIONS II-A, II-B and II-C
CLEAR CONDITIONING SHAMPOOS

| | % By Wt. | | |
|---|---|---|---|
| | Formulation II-A | Formulation II-B | Formulation II-C |
| Ingredients (INCI) | Ref. #: (122-236) | (222-237) | (122-238) |
| Ammonium Lauryl Sulfate[1] | 15 | 15 | 15 |
| Sodium Cocoyl Isethionate | 10 | 10 | 10 |
| Quaternium 75 | 5 | 5 | 5 |
| Cocamide DEA | 5 | 5 | 5 |
| FINSOLV ® SLB-101 | — | 1.0 | — |
| FINSOLV ® SLB-201 | — | — | 1.0 |
| DMDM Hydantoin[2] | 0.1 | 0.1 | 0.1 |
| Water | q.s. 100 | q.s. 100 | q.s. 100 |

[1]Standapol ® A, Henkel Corp., Ambler, PA 19002.
[2]Lonza Inc., Fair Lawn, NJ 07610.

Procedure: Combine ingredients with stirring and heat (where necessary) to obtain a uniform, clear solution. When clear, fill into suitable containers.

TABLE II-A

PROPERTIES OF CLEAR CONDITIONING SHAMPOO
PREPARATIONS OF FORMULATIONS II-A, II-B AND II-C

| Shampoo Preparation | Appearance | Clarity | Viscosity (cps) |
|---|---|---|---|
| FORMULATION II-A (Control) | Clear, thin gel | Clear | 800 |
| FORMULATION II-B (Control + FINSOLV ® SLB-101) | Clear, thin gel | Clear | 380 |
| FORMULATION II-C (Control + FINSOLV ® SLB-201) | Clear, thin gel | Clear | 550 |

TABLE II-B

FOAM RESULTS OF CLEAR CONDITIONING SHAMPOO
PREPARATIONS OF FORMULATIONS II-A, II-B AND II-C

| Shampoo Preparation | Initial Volume Of Foam (mls) | Volume After 5 mins. (mls) | Foam Characteristics |
|---|---|---|---|
| Formulation II-A (Control) | 300 | 150 | Thin, loose, scattered. Disappeared quickly. Gaps in-between bubbles. |
| Formulation II-B (Control + FINSOLV ® SLB-101) | 450 | 300 | Thick, dense, stable foam. Compact. No gaps in-between bubbles. |
| Formulation II-C (Control + FINSOLV ® SLB-201) | 400 | 250 | Thick, dense stable foam. Compact. No gaps in-between bubbles. |

Procedure: 1% of the product was dissolved in 200 mls. of water and shaken in a 500 mls cylinder with 10 sets of shakes.

TABLE II-C

COMPARISON OF EFFECTS OF CLEAR CONDITIONING
SHAMPOO PREPARATIONS OF FORMULATION II-A,
II-B AND II-C ON HAIR TRESSES

|  | FORMULATION II-A (Control) | FORMULATION II-B (Control + FINSOLV ® SLB-101) | FORMULATION II-C (Control + FINSOLV ® SLB-201) |
|---|---|---|---|
| DRY COMB | 5 | 2 | 3 |
| WET COMB | 7 | 4 | 3 |
| DE-TANGLING | 6 | 3 | 2 |
| SHINE/GLOSS | 10 | 1 | 2 |
| DRY FEEL/HANDLE | 7 | 2 | 3 |

Note:
All measurements are on a scale of 1–10, with 1 = best and 10 = worst)

Procedure: Rinsed hair tresses under tap water for 15 seconds. Rinsed hair tresses were treated with shampoo. Mixed for 5 minutes. Removed the tressses and rinsed with tap water running on it for 15 seconds. Air dried. Performed wet and dry comb tests.

Clear and Mild Skin Cleansing Gel

Formulation III-A of Table III below is a common control formulation for Clear and Mild Skin Cleansing Gel (Ref. No. 122–246 Series). Formulations III-B and II-C of Table III are comparative formulations for the Clear and Mild Skin Cleansing Gel of Formulation III-A, the only differences being that 1.0% by wt. of Dimethicone Copolyol Benzoate is added, with comparable adjustments to the percentage of water added. In Formulation III-B, FINSOLV® SLB-101 is added, and in Formulation III-C, FINSOLV® SLB-201 is added. Table III-A compares foam results for skin cleansing gel preparations of Formulations III-A, III-B and III-C. Table III-B compares the effects of clear and mild skin cleansing gel preparations of Formulations III-A, III-B and III-C on skin cleansing.

TABLE III

FORMULATIONS III-A, III-B and III-C
CLEAR AND MILD SKIN CLEANSING GEL

| | % By Wt. | | |
|---|---|---|---|
| Ingredients (INCI) Ref. #: | Formulation III-A (122-246) | Formulation III-B (222-246-A) | Formulation III-C (122-246-B) |
| Ammonium Laureth 2 Sulfate[1] | 15.0 | 15.0 | 15.0 |
| Sodium Cocoyl Isethionate | 6.0 | 6.0 | 6.0 |
| Cocoamido Propyl Betaine | 20.0 | 20.0 | 20.0 |
| Glucamate SSE 20[3] | 2.0 | 2.0 | 2.0 |
| FINSOLV ® SLB-101[4] | — | 1.0 | — |
| FINSOLV ® SLB-201[5] | — | — | 1.0 |
| Germaben II | 0.5 | 0.5 | 0.5 |
| Fragrance | 0.1 | 0.1 | 0.1 |
| NaCl | 1.0 | 1.0 | 1.0 |
| Water | q.s. 100 | q.s. 100 | q.s. 100 |

[1]STANDAPOL ® ALES 2, Henkel Corp., Ambler, PA 19002.

Procedure: Combine the water, Ammonium Laureth 2 Sulfate and the Cocoamido Propyl Betaine at 55° C.–60° C. Add the TAURANOL® I-78C, stirring continuously until dissolved. Add Glucamate SSE 20, then the preservative (Germaben II), fragrance and salt. Mix. Pour warm.

TABLE III-A

FOAM RESULTS OF CLEAR AND MILD SKIN CLEANSING GEL
PREPARATIONS OF FORMULATIONS III-A, III-B AND III-C

| Gel Preparation | Initial Volume Of Foam (mls) | Volume After 5 mins. (mls) | Foam Characteristics |
|---|---|---|---|
| Formulation III-A (Control) | 300 | 100 | Thin, loose, scattered Not compact. Small bubbles. Loose foam. |
| Formulation III-B (Control + FINSOLV ® SLB-101) | 450 | 325 | Thick, dense, compact, large bubbles. Stable foam. |
| Formulation III-C (Control + FINSOLV ® SLB-201) | 400 | 300 | Thick, dense, compact, large bubbles. Stable foam. |

Procedure: 1% of the product was dissolved in 200 ml. of water and did the shake test in a 500 ml. cylinder with 10 sets of shakes. The clear and mild skin cleansing gels contain Sodium Cocoyl Isethionate, Ammonium Laureth 2 Sulfate, water, betaine. Sodium chloride and Glucamate SSE 20 were used as thickeners.

TABLE III-B

COMPARISON OF EFFECTS OF CLEAR AND MILD
SKIN CLEANSING GEL PREPARATIONS OF
FORMULATIONS III-A, III-B AND III-C ON SKIN CLEANSING

| Preparation | Feel, Wet and Dry |
|---|---|
| Formulation III-A (Control) | Good foam, but loose and not compact after drying. Heavy feel, sticky and greasy. |
| Formulation II-B (Control + FINSOLV ® SLB-101) | Thick, dense foam; foam compact after drying. Nice and silky feel. Gloss and shine. |
| Formulation II-C (Control + FINSOLV ® SLB-201) | Thick, dense foam; foam compact, not loose, after drying. Nice and silky feel. Gloss and shine. |

Clear and Mild Skin Cleansing Gel

Formulation IV-A of Table IV below is a common control formulation for Clear and Mild Skin Cleansing Gel (Ref. No. 122–247 Series). Formulations IV-B and IV-C of Table IV are comparative formulations for the Clear and Mild Skin Cleansing Gel of Formulation IV-A, the only differences being that 1.0% by wt. of Dimethicone Copolyol Benzoate is added, with comparable adjustments to the percentage of water added. In Formulation IV-B, FINSOLV® SLB-101 is added, and in Formulation IV-C, FINSOLV® SLB-201 is added. Table IV-A compares foam results for skin cleansing gel preparations of Formulations IV-A, IV-B and IV-C. Table IV-B compares the effects of clear and mild skin cleansing gel preparations of Formulations IV-A, IV-B and IV-C on skin cleansing.

TABLE IV

FORMULATIONS IV-A, IV-B and IV-C
CLEAR AND MILD SKIN CLEANSING GEL

| | % By Wt. | | |
|---|---|---|---|
| Ingredients (INCI) Ref. #: | Formulation IV-A (122-247) | Formulation IV-B (222-247-A) | Formulation IV-C (122-247-B) |
| Ammonium Laureth 2 Sulfate | 15.0 | 15.0 | 15.0 |
| Sodium Cocoyl Isethionate | 6.0 | 6.0 | 6.0 |
| Cocoamido Propyl Betaine | 20.0 | 20.0 | 20.0 |
| FINSOLV ® SLB-101 | — | 1.0 | — |
| FINSOLV ® SLB-201 | — | — | 1.0 |
| Crothix | 0.5 | 0.5 | 0.5 |
| Germaben II | 0.5 | 0.5 | 0.5 |
| Fragrance | 0.1 | 0.1 | 0.1 |
| Water | q.s. 100 | q.s. 100 | q.s. 100 |

Procedure: Combine the water, Ammonium Laureth 2 Sulfate and the Cocoamido Propyl Betaine at 55° C.–60° C. Add the TAURANOL® I-78C, stirring continuously until dissolved. Add Crothix, then the preservative (Germaben II) and fragrance. Mix. Pour warm.

TABLE IV-A

FOAM RESULTS OF CLEAR AND MILD SKIN CLEANSING GEL PREPARATIONS OF FORMULATIONS IV-A, IV-B AND IV-C

| Gel Preparation | Initial Volume Of Foam (mls) | Volume After 5 mins. (mls) | Foam Characteristics |
| --- | --- | --- | --- |
| Formulation IV-A (Control) | 250 | 150 | Thin, loose, scattered foam. Small bubbles. Lots of air in-between bubbles. |
| Formulation IV-B (Control + FINSOLV ® SLB-101) | 450 | 350 | Thick, dense, compact foam. Large bubbles. No air in-between bubbles. |
| Formulation IV-C (Control + FINSOLV ® SLB-101) | 350 | 300 | Thick, dense, compact, large bubbles. No air in-between bubbles. |

Procedure: 1% of the product was dissolved in 200 ml. of water and did the shake test in a 500 ml. cylinder with 10 sets of shakes. The clear and mild skin cleansing gels contain Sodium Cocoyl Isethionate, Ammonium Laureth 2 Sulfate, water, betaine. Crothix was used as a thickener.

TABLE IV-B

COMPARISON OF EFFECTS OF CLEAR AND MILD SKIN CLEANSING GEL PREPARATIONS OF FORMULATIONS IV-A, IV-B AND IV-C ON SKIN CLEANSING

| Preparation | Feel, Wet and Dry |
| --- | --- |
| Formulation IV-A (Control) | Not much foam; loose and airy bubbles. After drying, there was a heavy feel and stickiness. No shine or gloss. |
| Formulation IV-B (Control + FINSOLV ® SLB-101) | Thick, dense foam. Large bubbles, compact foam. After drying, nice and silky feel, with gloss and shine. |
| Formulation IV-C (Control + FINSOLV ® SLB-201) | Thick, dense foam; large bubbles, compact foam. After drying, nice and silky feel, with gloss and shine. No heavy feel or stickiness. |

Clear and Mild Skin Cleansing Gel

Formulation V-A of Table V below is a common control formulation for Clear and Mild Skin Cleansing Gel (Ref. No. 122–248 Series). Formulations V-B, V-C, V-D, V-E, and V-F of Table V are comparative formulations for the Clear and Mild Skin Cleansing Gel of Formulation V-A, the only differences being that 1.0% by wt. of Dimethicone Copolyol Benzoate is added, with comparable adjustments to the percentage of water added. In Formulation V-B, FINSOLV® SLB-101 is added; in Formulation V-C, FINSOLV® SLB-201 is added; in Formulation V-D, FINSOLV® PL-355 is added; in Formulation V-E, FINSOLV® PL-62 is added; in Formulation V-F, FINSOLV® EMG-20 is added. Table V-A compares foam results for skin cleansing gel preparations of Formulations V-A through V-F. Table V-B compares the effects of clear and mild skin cleansing gel preparations of Formulations V-A through V-F on skin cleansing.

TABLE V

FORMULATIONS V-A THROUGH V-F CLEAR AND MILD SKIN CLEANSING GEL

| | % By Wt. Formulations | | | | | |
| --- | --- | --- | --- | --- | --- | --- |
| | V-A | V-B | V-C | V-D | V-E | V-F |
| Ingredients (INCI) | (122-248) | (122-248-A) | (122-248-B) | (122-248-C) | (122-248-D) | (122-248-E) |
| Ammonium Laureth 2 Sulfate | 15.0 | 15.0 | 15.0 | 15.0 | 15.0 | 15.0 |
| Sodium Cocoyl Isethionate | 6.0 | 6.0 | 6.0 | 6.0 | 6.0 | 6.0 |
| Cocoamido Propyl Betaine | 20.0 | 20.0 | 20.0 | 20.0 | 20.0 | 20.0 |
| FINSOLV ® SLB-101 | — | 1.0 | — | — | — | — |
| FINSOLV ® SLB-201 | — | — | 1.0 | — | — | — |
| FINSOLV ® PL-355 | — | — | — | 1.0 | — | — |
| FINSOLV ® PL-62 | — | — | — | — | 1.0 | — |
| FINSOLV ® EMG-20 | — | — | — | — | — | 1.0 |
| Germaben II | 0.5 | 0.5 | 0.5 | 0.5 | 0.5 | 0.5 |
| Fragrance | 0.1 | 0.1 | 0.1 | 0.1 | 0.1 | 0.1 |
| Water | q.s. 100 | q.s. 100 | q.s. 100 | q.s. 100 | q.s. 100 | q.s. 100 |

Procedure: Combine the water, Ammonium Laureth 2 Sulfate and the Cocoamido Propyl Betaine at 55° C.–60° C. Add the TAURANOL® I-78C, stirring continuously until dissolved. Add the dimethicone copolyol benzoate. Add Germaben II and fragrance at 35° C. Mix. Pour warm.

TABLE V-A

FOAM RESULTS OF CLEAR AND MILD SKIN CLEANSING GEL PREPARATIONS OF FORMULATIONS V-A THROUGH V-F

| Gel Preparation | Initial Volume Of Foam (mls) | Volume After 5 mins. (mls) | Foam Characteristics |
|---|---|---|---|
| Formulation V-A (Control) | 300 | 200 | Thin, loose, scattered foam. Airy bubbles. Not compact. |
| Formulation V-B (Control + FINSOLV ® SLB-101) | 450 | 325 | Thick, dense, compact foam. No air in-between bubbles. |
| Formulation V-C (Control + FINSOLV ® SLB-201) | 400 | 300 | Thick, dense, compact foam. Large bubbles. No air in-between bubbles. |
| Formulation V-D (Control + FINSOLV ® PL-355) | 375 | 300 | Loose foam. Medium sized bubbles. Not very compact. |
| Formulation V-E (Control + FINSOLV ® PL-62) | 350 | 250 | Loose foam. Small bubbles. Not dense. Not compact. |
| Formulation V-F (Control + FINSOLV ® EMG-20) | 375 | 200 | Loose, not compact foam. Air in-between bubbles. |

Procedure: 1% of the product was dissolved in 200 ml. of water and did the shake test in a 500 ml. cylinder with 10 sets of shakes. The clear and mild skin cleansing gels contain Sodium Cocoyl Isethionate, Ammonium Laureth 2 Sulfate, water, betaine. No thickeners were used.

In conclusion, Formulations V-B and V-C, which are invention examples, gave superior foam characteristics over control formulations and other benzoate ester formulations.

TABLE V-B

COMPARISON OF EFFECTS OF CLEAR AND MILD SKIN CLEANSING GEL PREPARATIONS OF FORMULATIONS V-A THROUGH V-F ON SKIN CLEANSING

| Preparation | Feel, Wet and Dry |
|---|---|
| Formulation V-A (Control) | Thin foam; compact bubbles. After drying, some heavy feel and stickiness. No shine or gloss. |
| Formulation V-B (Control + FINSOLV ® SLB-101 | Creamy large bubbles, foamy. Dense, compact foam. After drying, nice, silky, soft feel, with very high gloss and shine. No sticky or heavy feel at all. |
| Formulation V-C (Control + FINSOLV ® SLB-201) | Creamy, large bubbles; foamy. Compact and dense foam. After drying, no heavy feel or stickiness. |
| Formulation V-D (Control + FINSOLV ® PL-355) | Small bubbles, but not compact. Thin foam. After drying, some stickiness and little heaviness. No gloss or shine. |
| Formulation V-E (Control + FINSOLV ® PL-62) | Small bubbles but not compact. Medium foam. After drying, some heaviness. No gloss or shine. |
| Formulation V-F (Control + FINSOLV ® EMG-20) | Thin foam, but not compact. No stickiness after drying. No gloss or shine. |

In conclusion, Formulations V-B and V-C, which are invention examples, are superior in skin feel as compared to other benzoate esters.

Pearlescent Hand Soap

Formulation VI-A of Table VI below is a common control formulation for pearlescent hand soap. Formulations VI-B and VI-C of Table VI are comparative formulations for the pearlescent hand soap of Formulation VI-A, the only differences being that 1.0% by wt. of Dimethicone Copolyol Benzoate is added, with comparable adjustments to the percentage of water added. In Formulation VI-B, FINSOLV® SLB-101 is added, and in Formulation VI-C, FINSOLV® SLB-201 is added. Table VI-A compares the properties of pearlescent hand soap preparations of Formulations VI-A, VI-B, and VI-C. Table VI-B compares foam results for pearlescent hand soaps of Formulations VI-A, VI-B and VI-C. Table VI-C compares the effects of pearlescent hand soaps of Formulations VI-A, VI-B and VI-C on skin.

TABLE VI

FORMULATIONS VI-A, VI-B and VI-C PEARLESCENT HAND SOAP

| | % By Wt. | | |
|---|---|---|---|
| Ingredients (INCI) Ref. #: | Formulation VI-A (122-241) | Formulation VI-B (122-241-A) | Formulation VI-C (122-241-B) |
| A. Propylene Glycol | 5.00 | 5.00 | 5.00 |
| Hydroxypropyl Methylcellulose | 0.25 | 0.25 | 0.25 |
| B. Water | q.s. 100 | q.s. 100 | q.s. 100 |
| Propylene Glycol | 10.00 | 10.00 | 10.00 |
| Glycol Stearate | 2.00 | 2.00 | 2.00 |
| C. Sodium Cocoyl Isethionate | 20.00 | 20.00 | 20.00 |
| FINSOLV ® SLB-101 | — | 1.0 | — |
| FINSOLV ® SLB-201 | — | — | 1.0 |

Procedure:

1. Slurry gum (Hydroxypropyl methylcellulose) in propylene glycol and add to (B), and heat to 85° C.
2. Add (C) and when dissolved, add FINSOLV®t SLB-101 or FINSOLV® SLB-201, discontinue heating and cool to room temperature with mixing.

TABLE VI-A

PROPERTIES OF PEARLESCENT HAND SOAP PREPARATIONS OF FORMULATIONS VI-A, VI-B AND VI-C

| Hand Soap Preparation | Appearance | Viscosity (cps) |
|---|---|---|
| FORMULATION VI-A (Control) | Soft paste | 7400 |
| FORMULATION VI-B (Control + FINSOLV ® SLB-101) | Soft paste | 5400 |
| FORMULATION VI-C (Control + FINSOLV ® SLB-201) | Soft paste | 6000 |

TABLE VI-B

FOAM RESULTS OF PEARLESCENT HAND SOAP PREPARATIONS OF FORMULATIONS VI-A, VI-B AND VI-C

| Hand Soap Preparation | Initial Volume Of Foam (mls) | Volume After 5 mins. (mls) | Foam Characteristics |
|---|---|---|---|
| Formulation VI-A (Control) | 350 | 100 | Thin, loose, scattered foam. Not stable. Disappears fast. |
| Formulation VI-B (Control + FINSOLV ® SLB-101) | 450 | 325 | Thick, dense, compact foam. Stable. No air gaps in-between bubbles. |
| Formulation VI-C (Control + FINSOLV ® SLB-201) | 400 | 300 | Thick, dense, compact foam. Stable. No air gaps in-between bubbles. |

Procedure: 1% of the product was dissolved in 200 mls. of water and shaken in a 500 mls cylinder with 10 sets of shakes.

TABLE VI-C

COMPARISON OF EFFECTS OF PEARLESCENT HAND SOAP PREPARATIONS OF FORMULATION VI-A, VI-B AND VI-C ON SKIN

| Preparation | Feel, Wet and Dry |
|---|---|
| Formulation VI-A (Control) | Not much foam; not compact. After drying, there was a sticky feel. No shine or gloss after drying. |
| Formulation VI-B (Control + FINSOLV ® SLB-101) | Thick and rich foam. Large bubbles. After drying, nice and soft feel, with gloss and shine. No stickiness. |
| Formulation VI-C (Control + FINSOLV ® SLB-201) | Thick, dense foam. Large bubbles. After drying, nice, soft and silky feel, with gloss and shine. No stickiness. |

Procedure: Hand wash under running tap water for evaluation.
Soap Bar Evaluation
Ref. No. (125–81)

An evaluation of the uses of the novel benzoates of hydroxyl terminated polyether polysiloxane copolyols in bar soaps was conducted as described below. The results show improvements in the properties of bar soaps upon inclusion of the novel benzoates of the invention.

Soap bars containing syndet base FINEBASE 201 (Finetex, Inc., Elmwood Park N.J. 07407) have the following features during processing of the soap bars and after washing with said bars:

1. Runs well in the extruder
2. Good body with consistency, transparent or pearlescent effect.
3. Good body texture.
4. When using the bar to wash hands with water, it gives a creamy foam, with large, but not compact bubbles.
5. After drying, a soft feel was observed, with no stickiness, but with no gloss or shine observed either.

To the above soap bar containing syndet base FINEBASE 201 (Finetex, Inc., Elmwood Park N.J. 07407) was added 0.25% FINSOLV® SLB-101 or 0.25% FINSOLV® SLB-201. The typical processing was followed, i.e., FINEBASE 201 was added to the amalgamator., with 0.25% FINSOLV® SLB-101 or SLB-201, fragrance was incorporated, and the bar colored and refined as usual. The resulting bar was found to have additional beneficial properties in addition to those properties described above for the control bar.

A. Syndet Bar containing FINSOLV® SLB-101 was found to run excellently in the extruder; have excellent body with better consistency than the control bar; have excellent transparent or pearlescent effect; have excellent body texture. When washed with water, the bar produced dense, creamy foam, with large, compact and dense bubbles. A slippery feel was observed when the bar was wet. After drying, no stickiness was found on the skin. It had a nice, soft, silky feel and excellent shine and gloss was observed. The skin felt well-moisturized.

B. Syndet Bar containing FINSOLV® SLB-201 was also found to run excellently in the extruder; have excellent body with better consistency than the control bar; have excellent transparent or pearlescent effect; with excellent body texture. When washed with water, the bar produced thick, rich, creamy foam, with medium sized, semi-dense bubbles. The bar had a less slippery feel during washing as compared to the bar which included FINSOLV® SLB-101. After drying, no stickiness was found on the skin. A nice, soft, silky feel was observed on the skin, with excellent shine and gloss on the skin. The skin felt well-moisturized.

It is understood that the embodiments described herein are merely exemplary and that a person skilled in the art may make many variations and modifications without departing from the spirit and scope of the invention. All such modifications and variations are intended to be included within the scope of the invention described herein.

We claim:

1. A benzoate ester of hydroxyl terminated polyether polysiloxane copolyol having the following structure:

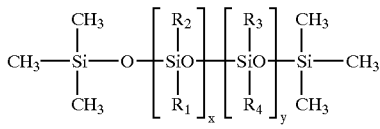

wherein x and y are integers which independently range from 1 to 50;

$R_1$, $R_2$, $R_3$ and $R_4$ may all be the same or different, provided that at least one of $R_1$, $R_2$, $R_3$ or $R_4$ is a hydroxyl terminated polyether group;

provided that when one of $R_1$, $R_2$, $R_3$ and $R_4$ is a hydroxyl terminated polyether, the others of $R_1$, $R_2$, $R_3$ and $R_4$ are selected from the group consisting of alkyl, aryl, alkaryl, aralkyl, alkoxy, substituted alkyl, substituted aryl, and mixtures thereof;

and wherein the hydroxyl terminated polyether group has been esterified with Benzoic Acid and has the structure

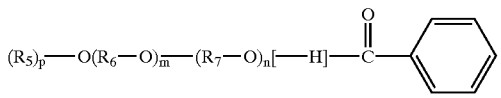

wherein $R_5$ is an alkyl group of one to ten carbon atoms; p is a number from one to ten; $R_6$ is an alkyl group of from two to twelve carbon atoms; m is a number from one to fifty; $R_7$ is an alkyl group of from two to twenty carbon atoms; and n is a number from one to fifty.

2. The benzoate ester of claim 1 wherein at least one of $R_1$, $R_2$, $R_3$ or $R_4$ is preferably a hydroxyl terminated co-polyether group wherein one polyether group comprises ethylene oxide groups and the other polyether group comprises propylene oxide groups or mixtures thereof.

3. The benzoate ester of claim 1 wherein $R_1$, $R_2$, $R_3$ and $R_4$ is preferably methyl or di-methyl provided that at least one of $R_1$, $R_2$, $R_3$ and $R_4$ is a hydroxyl terminated polyether copolyol radical.

4. The benzoate ester of claim 1 wherein said polyether polysiloxane copolyol has the following structure:

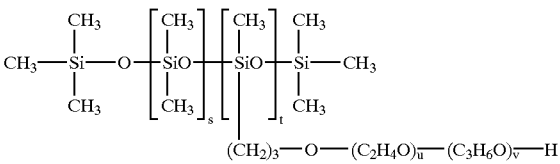

wherein $R_1$, $R_2$, and $R_3$ are methyl groups and wherein s, t, u and v are each independently an integer of 1 or greater.

5. The benzoate ester of claim 1 wherein said polyether polysiloxane copolyol has the following structure:

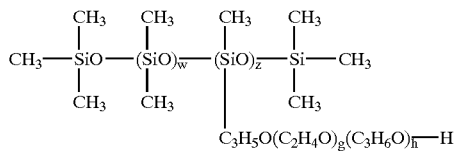

wherein w and z are each independently an integer ranging from about 1 to 20 and g and h are each independently an integer ranging from about 1 to 50.

6. A benzoate ester of hydroxyl terminated polyether polysiloxane copolyol having the following structure:

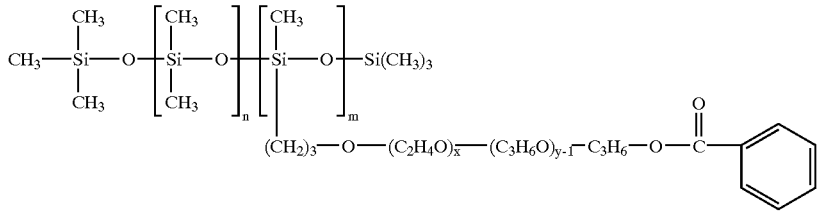

wherein n, m, x, and y are each independently an integer ranging from 1 to 50.

7. A benzoate ester of hydroxyl terminated polyether polysiloxane copolyol having the following structure:

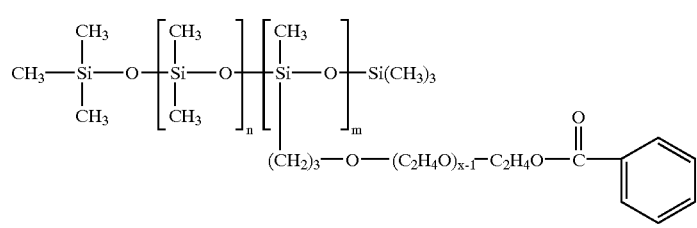

wherein n, m, and x are each independently an integer ranging from 1 to 50.

8. The benzoate ester of claim 6 which is prepared by the esterification of an aromatic monocarboxylic acid and hydroxyl terminated polyether polysiloxane copolyol having the following structure:

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n\left[\underset{\underset{(CH_2)_3-O-(C_2H_4O)_{\overline{x}}-(C_3H_6O)_{y-1}-C_3H_6OH}{|}}{\overset{\overset{CH_3}{|}}{Si}}-O\right]_m Si(CH_3)_3$$

wherein n, m, x, and y are each independently an integer ranging from 1 to 50.

9. A method of preparing the benzoate ester of claim 7 comprising reacting benzoic acid with hydroxyl terminated polyether polysiloxane copolyol having the following structure:

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n\left[\underset{\underset{(CH_2)_3-O-(C_2H_4O)_{x-1}-(C_2H_4OH)}{|}}{\overset{\overset{CH_3}{|}}{Si}}-O\right]_m Si(CH_3)_3$$

wherein n, m, and x are each independenty an integer ranging from 1 to 50.

10. A conditioning shampoo comprising an effective amount of the benzoate ester of claim 1.

11. A hair conditioner comprising an effective amount of the benzoate ester of claim 1.

12. A sunscreening composition comprising an effective amount of the benzoate ester of claim 1.

13. A liquid or solid soap comprising an effective amount of the benzoate ester of claim 1.

14. A skin care lotion comprising an effective amount of the benzoate ester of claim 1.

15. A process for treating fiber comprising contacting the fiber with an effective conditionng amount of the benzoate ester of claim 1.

16. The process of claim 15 wherein said contacting is in the presence of water.

17. The process of claim 15 wherein said effective conditioning amount ranges from 0.1 to 50.0% by weight in an aqueous dispersion, emulsion, solution, or in a solvent.

18. The process of claim 15 wherein said effective conditioning amount ranges from 0.1 to 5.0% by weight in an aqueous dispersion, emulsion, solution, or in a solvent.

19. The process of claim 15 wherein said effective conditioning amount ranges from 0.1 to 1.0% by weight in an aqueous dispersion, emulsion, solution, or in a solvent.

20. The process of claim 15 wherein said fiber is hair.

21. The process of claim 15 wherein said fiber is a synthetic or natural textile fiber.

22. A process for conditioning skin comprising contacting the skin with an effective conditioning amount of a benzoate ester of claim 1.

23. The process of claim 22 wherein said effective conditioning amount ranges from 0.1 to 50% by weight in an aqueous dispersion, emulsion, solution, or in a solvent.

24. The process of claim 22 wherein said effective conditioning amount ranges from 0.1 to 5.0% by weight in an aqueous dispersion, emulsion, solution, or in a solvent.

25. The process of claim 22 wherein said effective conditioning amount ranges from 0.1 to 1.0% by weight in an aqueous dispersion, emulsion, solution, or in a solvent.

26. A method for cleaning or conditioning human hair or skin comprising applying an effective amount of a cleaning or conditioning composition comprising from about 0.1 to 50% by weight of the benzoate ester of claim 1 to the hair or skin and then rinsing said composition from said hair or skin.

27. A method for conditioning hair comprising applying the benzoate ester of claim 1 to rinsed, wet hair subsequent to shampooing, and then rinsing said composition from the hair.

28. A conditioning shampoo comprising an effective amount of the benzoate ester of claim 6.

29. A hair conditioner comprising an effective amount of the benzoate ester of claim 6.

30. A sunscreening composition comprising an effective amount of the benzoate ester of claim 6.

31. A liquid or solid soap comprising an effective amount of the benzoate ester of claim 6.

32. A skin care lotion comprising an effective amount of the benzoate ester of claim 6.

33. A process for treating fiber comprising contacting the fiber with an effective conditioning amount of the benzoate ester of claim 6.

34. The process of claim 33 wherein said contacting is in the presence of water.

35. The process of claim 33 wherein said effective conditioning amount ranges from 0.1 to 50.0% by weight in an aqueous dispersion, emulsion, solution, or in a solvent.

36. The process of claim 33 wherein said effective conditioning amount ranges from 0.1 to 5.0% by weight in an aqueous dispersion, emulsion, solution, or in a solvent.

37. The process of claim 33 wherein said effective conditioning amount ranges from 0.1 to 1.0% by weight in an aqueous dispersion, emulsion, solution, or in a solvent.

38. The process of claim 33 wherein said fiber is hair.

39. The process of claim 33 wherein said fiber is a synthetic or natural textile fiber.

40. A process for conditioning skin comprising contacting the skin with an effective conditioning amount of a benzoate ester of claim 6.

41. The process of claim 40 wherein said effective conditioning amount ranges from 0.1 to 50% by weight in an aqueous dispersion, emulsion, solution, or in a solvent.

42. The process of claim 40 wherein said effective conditioning amount ranges from 0.1 to 5.0% by weight in an aqueous dispersion, emulsion, solution, or in a solvent.

43. The process of claim 40 wherein said effective conditioning amount ranges from 0.1 to 1.0% by weight in an aqueous dispersion, emulsion, solution, or in a solvent.

44. A method for cleaning or conditioning human hair or skin comprising applying an effective amount of a cleaning or conditioning composition comprising from about 0.1 to 50% by weight of the benzoate ester of claim 6 to the hair or skin and then rinsing said composition from said hair or skin.

45. A method for conditioning hair comprising applying the benzoate ester of claim 6 to rinsed, wet hair subsequent to shampooing, and then rinsing said composition from the hair.

46. A conditioning shampoo comprising an effective amount of the benzoate ester of claim 7.

47. A hair conditioner comprising an effective amount of the benzoate ester of claim 7.

48. A sunscreening composition comprising an effective amount of the benzoate ester of claim 7.

49. A liquid or solid soap comprising an effective amount of the benzoate ester of claim 7.

50. A skin care lotion comprising an effective amount of the benzoate ester of claim 7.

51. A process for treating fiber comprising contacting the fiber with an effective conditioning amount of the benzoate ester of claim 7.

52. The process of claim 51 wherein said contacting is in the presence of water.

53. The process of claim 51 wherein said effective conditioning amount ranges from 0.1 to 50.0% by weight in an aqueous dispersion, emulsion, solution, or in a solvent.

54. The process of claim 51 wherein said effective conditioning amount ranges from 0.1 to 5.0% by weight in an aqueous dispersion, emulsion, solution, or in a solvent.

55. The process of claim 51 wherein said effective conditioning amount ranges from 0.1 to 1.0% by weight in an aqueous dispersion, emulsion, solution, or in a solvent.

56. The process of claim 51 wherein said fiber is hair.

57. The process of claim 51 wherein said fiber is a synthetic or natural textile fiber.

58. A process for conditioning skin comprising contacting the skin with an effective conditioning amount of a benzoate ester of claim 7.

59. The process of claim 58 wherein said effective conditioning amount ranges from 0.1 to 5.0% by weight in an aqueous dispersion, emulsion, solution, or in a solvent.

60. The process of claim 58 wherein said effective conditioning amount ranges from 0.1 to 5.0% by weight in an aqueous dispersion, emulsion, solution, or in a solvent.

61. The process of claim 58 wherein said effective conditioning amount ranges from 0.1 to 1.0% by weight in an aqueous dispersion, emulsion, solution, or in a solvent.

62. A method for cleaning or conditioning human hair or skin comprising applying an effective amount of a cleaning or conditioning composition comprising from about 0.1 to 50% by weight of the benzoate ester of claim 6 to the hair or skin and then rinsing said composition from said hair or skin.

63. A method for conditioning hair comprising applying the benzoate ester of claim 7 to rinsed, wet hair subsequent to shampooing, and then rinsing said composition from the hair.

* * * * *